United States Patent [19]

Sturm et al.

[11] Patent Number: 4,640,281
[45] Date of Patent: Feb. 3, 1987

[54] TOURNIQUET

[75] Inventors: Gerd-Jochen Sturm, Leverkusen; Wolfgang Wehking, Cologne, both of Fed. Rep. of Germany

[73] Assignee: Prämeta Präzisionsmetall- und Kunststofferzeugnisse G. Baumann & Co., Cologne, Fed. Rep. of Germany

[21] Appl. No.: 806,977

[22] Filed: Dec. 9, 1985

[30] Foreign Application Priority Data

Dec. 15, 1984 [DE] Fed. Rep. of Germany ....... 3445794
Oct. 30, 1985 [DE] Fed. Rep. of Germany ....... 3538583

[51] Int. Cl.$^4$ ............................................. A61B 17/12
[52] U.S. Cl. ................................ 128/327; 24/115 G; 24/115 M
[58] Field of Search ........... 128/327; 24/68 CD, 71.2, 24/115 G, 115 M, 136 L

[56] References Cited

U.S. PATENT DOCUMENTS 3,958,575  5/1976  Von Soiron ................. 128/327
4,125,115 11/1978  Mayo et al. ................ 128/327
4,561,437 12/1985  Kirchner .................... 128/327

FOREIGN PATENT DOCUMENTS 121461  1/1927  Switzerland ............... 24/71 ST

Primary Examiner—Albert J. Makay
Assistant Examiner—David W. Westphal
Attorney, Agent, or Firm—Diller, Ramik & Wight

[57] ABSTRACT

A tourniquet including a belt and buckle with the buckle being formed of first and second buckle parts with a first end belt being connected to the first buckle part formed in a loop, and a second end thereof being releasably clamped between the first and second buckle parts; a pair of pivot pins of the first buckle part being received in recesses of the second buckle part for assembling these parts and maintaining the same in pivotal relationship to each other, and a cam operative upon relative sliding motion between the first and second buckle parts to automatically pivot the buckle parts to clamp the second belt in therebetween. In another embodiment the clamping effect is created by utilizing the elastic force of the belt which acts against a projecting portion of the first buckle belt to pivot the same to its clamping position.

20 Claims, 10 Drawing Figures

TOURNIQUET

BACKGROUND OF THE INVENTION

This invention relates to a tourniquet formed by a belt and a belt buckle with the belt having a loop adapted to constrict blood vessels when placed upon the limb of a person in a well known manner.

SUMMARY OF THE INVENTION

The buckle is formed of two buckle parts, namely, a first upper buckle part carrying a pair of oppositely directed pivot pins and a second lower buckle part having upstanding side walls, each with a recess, for slidably receiving and pivotably mounting therein the pivot pins. One end of the belt is connected to an end of the upper part, formed into a loop, and then arranged in slidable relationship between the upper buckle part and the lower buckle part with an end of the upper buckle part opposite the connection thereof to the belt having a clamping tongue. As the upper buckle part is pivoted, the clamping tongue is brought into clamping engagement with the end of the belt remote from the belt loop. Heretofore, in tourniquets of this type a spring has been used to provide the pivoting of the upper buckle part to achieve the clamping action and thereby retain the loop in its constricting relationship to the limb. In the present invention a spring is totally unnecessary, yet the buckle can perform as intended, clamp and unclamp the belt between the two buckle parts and rapidly assemble and disassemble the two buckle parts to quickly form or unform the loop, as, for example, when respectively applying and removing the tourniquet to the limb.

In further accordance with this invention, the lower buckle part preferably has a pair of upstanding sides, each of which includes a recess open at one end and closed at its opposite end into which oppositely directed pins of the upper buckle part can be received for relatively assembling the upper and lower buckle parts to each other and disassembling the same. When the buckle parts are pivoted relative to each other, the buckle can be locked and unlocked, while when the buckle parts are slid relative to each other, the buckle parts can be disassembled.

In keeping with the present invention, preferably the lower buckle part includes a base and two upstanding sides, each provided with a recess having a blind end with the latter serving as a pintle for each of the projecting pins of the upper buckle part which in turn includes a locking cam or tongue to one side of the pivot pins and a projection at the opposite end of the upper buckle part in the immediate area of the attachment of the belt thereto. In one embodiment of the invention, the lower buckle part includes one or a pair of spaced cams which react against the projecting portion as the belt buckles are assembled by sliding the pivot pins along the recesses until the pins are housed at the recess ends. During this assembly, the projection rides along a cam surface and automatically pivots the upper buckle part in a direction to bring the tongue into gripping engagement with an end of the belt remote from the loop. By this structural arrangement of parts, the belt is gripped between the buckle parts in the absence of any type of spring for either moving these parts or maintaining assembly therebetween, as is known in the prior art.

In keeping with another embodiment of this invention, the projecting portion of the upper buckle part is spaced a predetermined distance from an upper surface of the base plate of the lower buckle part, and the belt has a thickness larger than the latter and is made of elastic material. A portion of the belt adjacent the loop is sandwiched between the upper surface of the base and the projecting portion and, thus, the elasticity of the belt alone creates the force for pivoting the upper buckle part to bring the tongue thereof into clamping relationship to the belt, thereby maintaining the loop in constricting engagement relative to the limb of a patient.

Thus, the belt and particularly the elasticity thereof results in the clamping pressure, again in the absence of conventional springs.

In both embodiments of the invention the recesses for receiving the pivot pins are of a relatively straightforward construction but are appropriately tapered to reliably insure that the buckle parts are maintained in assembled relationship, yet are readily intentionally disassembled. This is created by back-tapering the angles of the recesses and the end of each recess relative to each other and to the cam surface in the first embodiment of the invention. In one case, the recesses open in a direction away from the loop or the belt and to disassemble the buckle parts the upper buckle part must be moved toward the loop which automatically not only releases the restraining or tightening effect of the loop upon a limb but results in the subsequent disassembly of the buckle parts in a natural, simple and relatively timewise efficient manner. However, the recess may likewise be inclined to the vertical opening toward the base of the lower buckle part with a slight taper in a direction away from the loop so that the upper buckle part must be raised slightly upwardly and toward the loop before being pulled away from the loop to disassemble the buckle parts. In this case the loop is tightened slightly before it is totally loosened upon the buckle parts being disassembled.

In a further embodiment of the invention, the cams which react with the projecting portion of the upper buckle part to result in the clamping action of the tongue are preferably spaced from each other. Thus, the belt which is made of flexible material, can be inserted between the spacing of these cams to underlie the same between the cams and the base plate of the lower buckle part. This permits the belt to be readily assembled to and disassembled from the lower buckle part. However, in lieu of the two spaced cams a single cam may be utilized, and in this case the belt would have to be threaded endwise between the single bridging cam and the lower base plate of the lower buckle part. In either case the upper surface of the cam or cams is the camming surface and the same is preferably inclined slightly to the horizontal at an angle diverging toward the belt clamping tongue of the upper buckle part. Thus, as the pins are slid into the recesses, the projecting portion of the upper buckle part is progressively pivoted to bring the tongue into clamping engagement with the belt.

With the above and other objects in view that will herinafter appear, the nature of the invention will be more clearly understood by reference to the following detailed description, the appended claims and the several views illustrated in the accompanying drawings.

BRIEF DESCRIPTION OF THE DRAWINGS

FIGS. 1 through 4 is a cross-sectional view taken generally along line VIII—VIII of FIG. 1, and illustrates a spring tongue carried by a bar of the belt for retaining the belt assembled to the upper buckle part.

DESCRIPTION OF THE PREFERRED EMBODIMENTS

Figure 1:
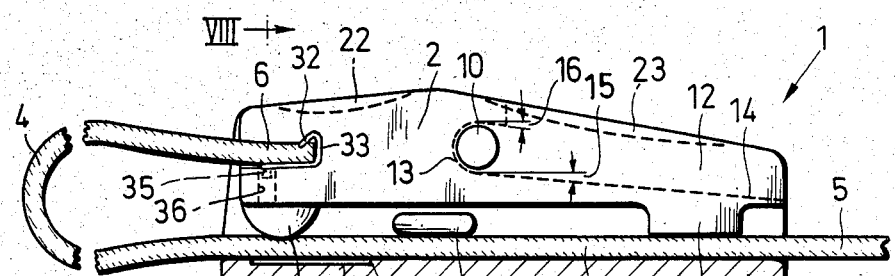
FIG. 1 is a longitudinal sectional view through a tourniquet of the present invention and illustrates a belt, a pair of buckle parts of a buckle, and interengaged pivot pins and recesses of the buckle parts.

A novel tourniquet constructed in accordance with this invention is illustrated in FIGS. 1 through 4 and 8 and is generally designatated by the reference numeral 1.

The tourniquet 1 includes a belt buckle formed of an upper or first buckle part 2 and a lower or second buckle part 3 which are slidable assembled and disassembled to each other and can pivot relative to each other, as will be described more fully hereinafter.

The buckle parts are designed specifically to maintain a loop 4 of an elastic belt 5 entrained about the limb of a patient to constrict the blood vessels thereof in a conventional manner.

Figure 2:
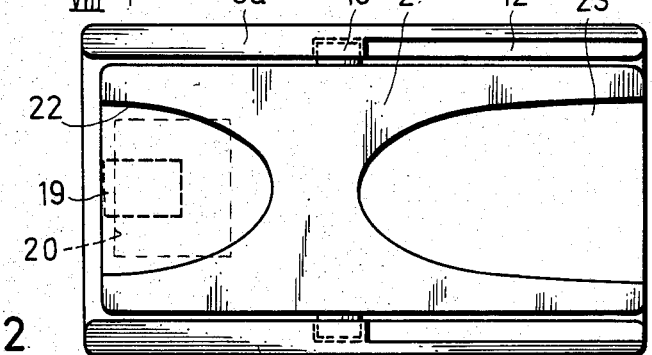
FIG. 2 is a top plan view of the buckle of FIG. 1 and illustrates both pivot pins, both recesses and a shallow hollow or recess underlying and aligned with the projecting portion of the first buckle part.
Figure 3:
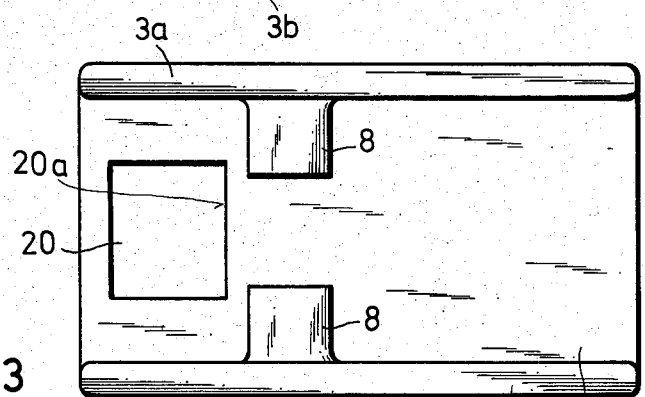
FIG. 3 is a top plan view of the lower buckle part and illustrates a pair of opposing bars spaced from each other between which the belt can be inserted so as to be positioned as shown in FIG. 1.
Figures 4, 8:
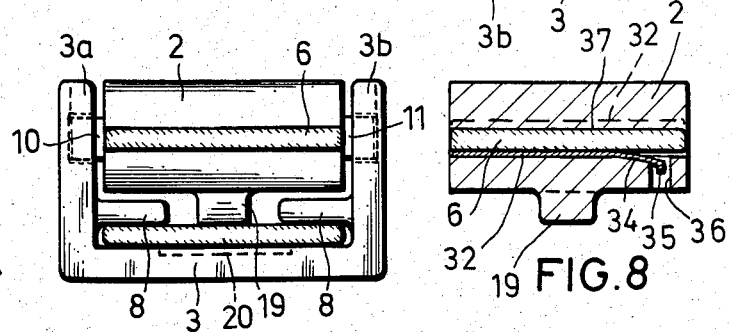
FIG. 4 is an end view looking from the left in FIG. 1 and illustrates the location of the projecting portion of the upper buckle part between the spaced bars of the lower buckle parts and the belt.
FIG. 8 which appears on the sheet of drawing containing

The lower buckle part 3 includes a base or base plate (unnumbered) from either side which projects a pair of upstanding side walls 3a, 3b (FIG. 2). The upper buckle part 2 is essentially housed between the side walls 3a, 3b, as is best illustrated in FIG. 2. The belt 5 includes a first end 6 adjacent the loop 4 which is sidewise or laterally inserted in a back-tapered slot or recess 33 of a front end portion (unnumbered) of the upper buckle part 2. The belt end 6 carries a metallic channel member 32 which is formed of spring sheet material and is crimped into engagement with the belt end 6, as is readily apparent from FIG. 1. The channel member 32 prevents the belt end 76 from being longitudinally withrawn from the channel 33, although lateral withdrawal is possible, as will be described more fully herinafter.

The belt 5 also includes another opposite end 7 which basically is sandwiched between the upper buckle part 2 and the lower buckle part 3, as is clearly illustrated in FIG. 1. The end 7 of the belt 5 passes beneath a pair of transversely spaced cross bars 8 (FIG. 3) projecting from the side walls 3a, 3b. Because of the interruption or spacing between the cross bars or bars 8, 8, an elastic, flexible belt can be inserted beneath the bars 8, 8 by simply folding the belt 5 transversely, inserting the edges downwardly into the space between the bars 8, 8 and then allowing the transverse edges to simply slide transversely toward the slide walls 3a, 3b until the belt is completely sandwiched between the bars 8, 8 and the base plate (unnumbered) of the lower buckle part 3. The latter construction is very advantageous because most tourniquet belts 5 have stops or enlargements at each of the ends thereof, such as the channel member 33 which preclude the belts from being withdrawn endwise through the buckle. In this case, the belt can be quickly removed from the lower buckle part 3 by simply pulling the same through the space between the bars 8, 8.

Interengaged pivot pin and recess means are provided for cooperatively slidably securing and releasing the buckle parts 2, 3 relative to each other and for effecting pivotal movement therebetween. The interengaged pivot pin and recess means are formed by pivot pins 10, 11 (FIGS. 1 and 4) projecting from opposite lateral sides (unnumbered) of the upper buckle part 2 which are received in recesses 12 (FIGS. 1 and 2) of each of the side walls 3a, 3b. The recesses 12 are generally longitudinally extending notches closed along a lower or bottom edge 14 and opened along the upper side thereof (FIG. 2) except for generally semi-cylindrical ends 13 of the recesses 12 which form bearing or pivotal surfaces for the pins 10, 11. Each lower edge 14 defines with the horizontal an angle 15 while each relatively short upper edge (unnumbered) of the recess 12 adjacent the end 13 defines with the horizontal an included angle 16. The angle 16 is slightly larger than the angle 15 so that the pins 10, 11 must be basically forced past the relatively narrower distance between the apexes of these angles before snapping into the somewhat relieved end 13 of the recesses 12. Stated another way, the ends 13 of the recesses 12 have a diameter corresponding to the outside diameter of the pins 10, 11 whereby the convergence of the angles 15, 16 define a spacing slightly less than the diameter of the pins 10, 11 requiring that a slight force be used to move the pins 10, 11 into the ends 13 of the recesses 12. However, the same forceful insertion of the pins 10, 11 into the ends 13 of the recesses 12 prevents the accidental disassembly of the pins 10, 11 therefrom.

The upper buckle part 2 is provided at its right-hand end, as viewed in FIG. 1, with a downwardly projecting clamping cam or clamping tongue 18 which clamps against the belt end 7 and holds the same clamped when the upper buckle part 2 has been pivoted clockwise to its clamping position. At the opposite end of the upper buckle part 2 is a downwardly directed projection 19 having a lowermost surface (unnumbered) which engages against the belt 5 in the area of an upwardly facing cavity, hollow or recess 20. The distance between the lowermost surface of the projection 19 and the uppermost surface of the base plate (unnumbered) of the lower buckle part 3 is less than the cross-sectional thickness of the belt 5 and the end 7 thereof. Therefore, since the thickness of the belt 5, which is made of elastic or flexible material, is greater than the distance between the lower surface of the projection 19 and the upper surface of the base plate, the belt 5 will be compressed and the natural flexibility or elasticity of the belt directs forces upwardly through the projection or projecting portion 19 resulting in a clockwise moment of force and, thus, a clockwise pivoting of the upper buckle part 2 relative to the lower buckle part 3 about the pivot pins 10, 11. This clockwise pivoting brings the clamping tongue 18 into clamping action against the belt 5 to hold the loop 4 entrained about the limb of a patient. Hence, the selected distance heretofore described and the width of the belt combined with its elasticity functions as means for effectiing the automatic relative pivoting of the first upper and second lower buckle parts relative to each other to achieve the clamping action heretofore noted. If the belt 5 is of a greater thickness than that illustrated in FIG. 1, it will be possible to still accommodate the same because of the cavity or hollow 20. The belt will simply curve as it passes between the projecting portion 19 and through and in the hollow 20. Thus, the buckle 1 can be used with a variety of different widths of belts and when greater widths are used, the slight curvature imparted to the belt as it deflects into the hollow 20 additionally increases the force which might otherwise be applied to pull the end 7 to the left, as viewed in FIG. 1. This is simply because the belt must move through a curve in the area of the projecting portion 19 and the hollow 20, as opposed to a straight-line pulll as shown in FIG. 1.

In order to slide the upper buckle part 2 for assembly or disassembly, the upper wall (unnumbered) thereof (FIG. 2) is provided with a pair of gripping cavities 22, 23 which can be serrated or grooved to receive the fingers of a user to assist in pushing the upper buckle part 2 to the right (cavity 22 used) or to the left (cavity 23 used) relative to the illustration shown in FIGS. 1 and 2. In otherwords, if one places pressure in the area of the cavity 22 pushing the same to the right, the pivot pins 10, 11 will simply snap past the angled portions of the edges of the recesses 14 until they are completely released therefrom.

While the projecting portion 19 and the hollow cavity 20 are both shown to be of limited extent, each can span the entire transverse breadth of the lower base plate of the lower buckle part 3 between the side walls 3a, 3b. However, the clamping forces are sufficient when the projecting portion 19 is limited in its extent. If desired, a vertical edge 20a forming the rear edge of the hollow or cavity 20 may be inclined or tapered, and an opposite edge thereto (unnumbered) can be fully relieved so that the cavity or hollow 20 opens freely through the left side, as viewed in FIG. 1, of the lower base plate of the lower buckle part 3. In these cases, the elasticity of the belt 5 is still sufficient to obtain the clockwise pivoting as viewed in FIG. 1, to bring the clamping tongue 18 into clamping force against the end 7 of the belt 5.

Figure 5:
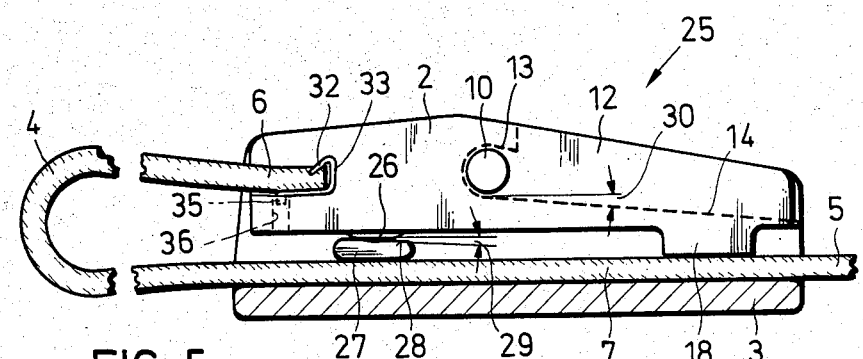
FIG. 5 is a longitudinal cross-sectional view of another tourniquet of this invention, and illustrates the manner in which upper surfaces of the bars or cams are tapered to form a camming surface reacting against a projecting portion of the upper buckle part to pivot the latter to bring the clamping tongue thereof into clamping engagement with the belt.
Figure 6:
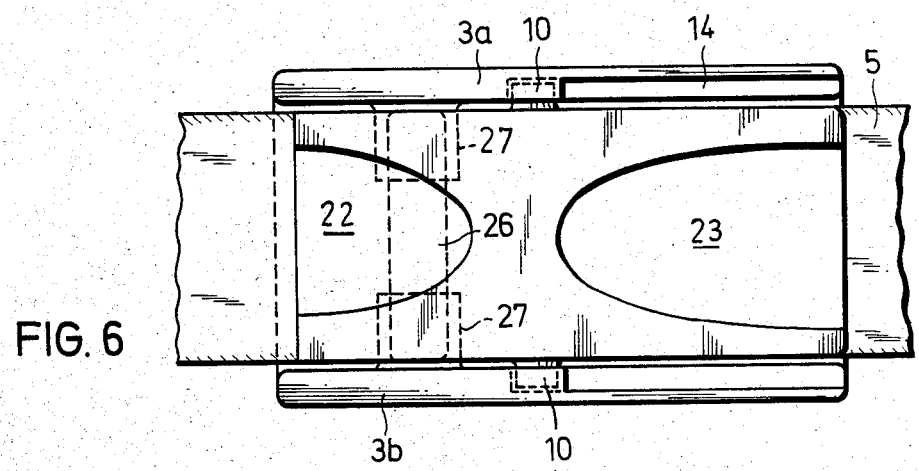
FIG. 6 is a fragmentary top plan view and illustrates details of the buckle.
Figure 7:
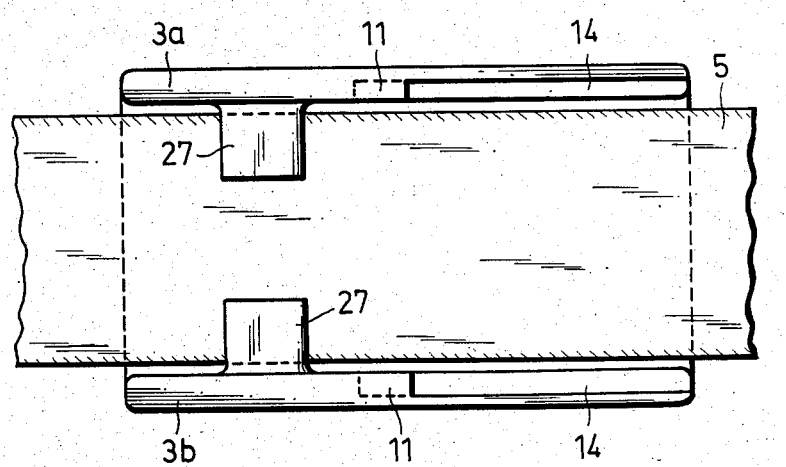
FIG. 7 is a fragmentary top plan view of the lower buckle part, and illustrates further details thereof.

Reference is now made to a tourniquet 25 of FIGS. 5 through 7 in which identical parts include reference numerals corresponding to those of the tourniquet 1. In this case, the upper belt buckle 2 also includes a projecting portion 26 similar to the projection portion 19 of the tourniquet 1, but of lesser vertical extent. When the buckle parts 2, 3 are assembled, the projecting portion or cross bar 26 contacts an upper camming surface 28 of each of the bars or cams 27. The upper surface 28 defines with the horizontal and included angle 29 which is somewhat smaller than an included angle 30 of the lower edge 14 of each recess 12 relative to the horizontal. Therefore, in order to bring the clamping tongue 18 in clamping engagement with the belt end 7, the pivot pins 10, 11 are moved from right-to-left along the recesses 14 and into the ends 13 of the recesses 14. As the latter occurs, the cross bar or cam follower 26 moves along the cam surface 28 creating a turning moment to pivot the upper buckle part 2 clockwise about the pivot pin 10, 11. The latter pivoting movement results in the continuing increase in the clamping force of the clamping tongue 18 applied to the belt end 7. Thus, assembly brings about simultaneous clamping action and vice versa. Furthermore, when the loop 4 is entrained about the limb of a patient, the elasticity of the loop 4 also creates a turning moment in a clockwise direction which further augments or increases the clamping force created at the tongue 18.

Figure 9:
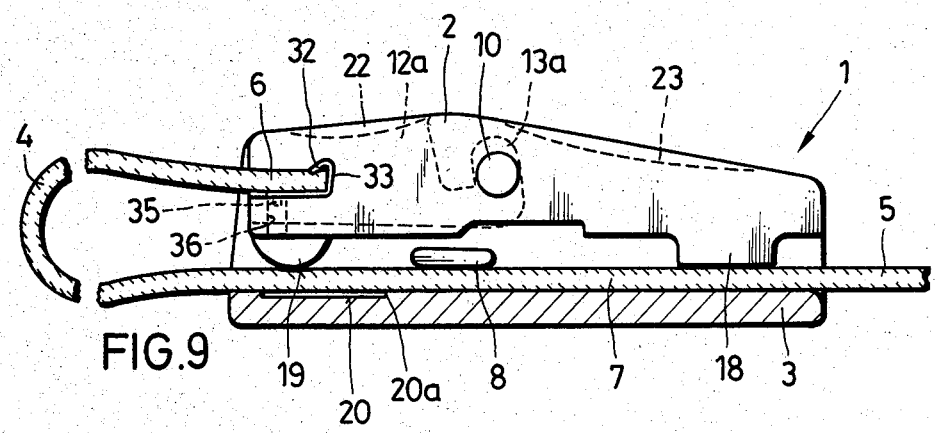
FIG. 9 is a longitudinal sectional view of another tourniquet similar to that shown in FIG. 1 with the major difference being the position and angulation of the relative recesses thereof which receive the pivot pins and permit the buckle parts to be readily assembled, disassembled and pivoted relative to each other.
Figure 10:
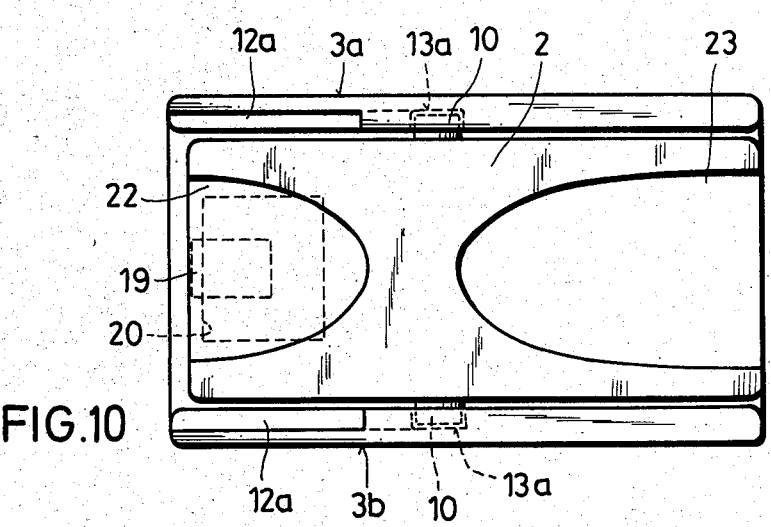
FIG. 10 is a top plan view of the buckle of FIG. 9 and illustrates further details thereof.

Reference is now made to FIGS. 9 and 10 of the drawings which illustrates another tourniquet which differs from tourniquet 1 of FIGS. 1 through 4 in the manner in which recesses 12a in the side walls 3a, 3b open in the direction toward the loop 4, rather than away from the loop 4, as in the tourniquet 1 of FIGS. 1 through 4. The recesses 12a each have an end 13a which is sloped to the vertical at a relatively shallow angle, opens downwardly, and inclines slightly toward the right-hand end of the buckle or toward the clamping tongue 18. This taper achieves the back-tapering earlier noted, but in order to release the upper buckle 2 it must first be moved downwardly, again as viewed best in FIG. 9 and then forwardly.

In all of the tourniquets heretofore described, each of the belt ends 6 carries the channel member 33 which additionally is formed of spring material and includes a spring tongue 34 having a short downwardly directed bent edge 35. The bent edge 35 is aligned with and is received in a bore or hole 36 of the buckle part 2 (FIG. 8) and is held therein under the snap action of the spring tongue 34 and the natural resilience of the metal of the overall channel member 32. The hole 36 is a through hole and, thus, is accessible from its bottom, as is evident in FIG. 8, so that a pin, nail, screwdriver or similar instrument can be inserted upwardly to deflect the bent edge 35 upwardly and release its locking relationship to the hole 36. After this has occurred, the end 6 of the belt 5 can be moved transversely out of the groove 32 leftward, as viewed in FIG. 8. Thus, the channel member 33 prevents the end 6 from being withdrawn longitudinaly from the groove 33 whereas the bent edge 35 prevents transverse removal thereof.

Instead of the spring or latching tongue 34, several such tongues can be provided directed toward different transverse sides of the belt end 6. When pulling the belt end 6 under a cross bar 8 or 27 which spans the totality of the side walls 3a, 3b and is not interrupted, as in FIG. 3, for example, the spring tongue can also press in the plane of the channel member 32. This permits the belt end to be easily pulled out from beneath such continuous cross bars 8. Thus, depending upon the particular formation of the cross bar or bars 8, continuous or spaced, the belt 5 can be easily changed at the belt buckle or upper buckle part 2.

Although in a preferred embodiment of the invention as has been specifically illustrated and described herein, it is to be understood that minor variations may be made in the application without departing from the spirit and scope of the invention, as defined in the appended claims.

What is claimed is:

1. A tourniquet comprising a belt and a buckle, said buckle having first and second buckle parts, means for connecting a first end of said belt to said first buckle part, means for releasably clamping a second end of said belt between said first and second buckle parts, a loop between said first and second belt ends, interengaged pivot pin and recess means for cooperatively slidably securing and releasing said first and second buckle parts and effecting pivotal movement therebetween, means for imparting relative pivotal movement between said first and second buckle parts to effect the clamping of said belt second end therebetween by said clamping means, said pivot pin means being positioned between said clamping means and said movement imparting means, and said pivotal movement imparting means being cam means operative upon relatively slidably securing said first and second buckle parts together to automatically relatively pivot said first and second buckle parts and thereby clamp said second belt end by said clamping means.

2. The tourniquet as defined in claim 1 wherein said recess means is closed in a direction toward said cam means and open in a direction toward said clamping means.

3. The tourniquet as defined in claim 1 wherein said recess means is open in a direction toward said cam means and closed in a direction toward said clamping means.

4. The tourniquet as defined in claim 1 wherein said recess means is closed in a direction toward said cam means and open in a direction toward said clamping means, and said recess means is inclined at an acute angle to the horizontal converging in a direction from said clamping means toward said pivot pin means.

5. The tourniquet as defined in claim 1 wherein said recess means is closed in a direction toward said cam means and open in a direction toward said clamping means, and said recess means is inclined at an acute angle to and below the horizontal converging in a direction from said clamping means toward said pivot pin means.

6. The tourniquet as defined in claim 1 wherein said recess means is open in a direction toward said cam means and closed in a direction toward said clamping means, said belt second end being disposed generally in sliding relationship between said first and second buckle parts, and said recess means have recess ends which open in a direction toward belt second end.

7. The tourniquet as defined in claim 1 wherein said recess means is open in a direction toward said cam means and closed in a direction toward said clamping means, said belt second end being disposed generally in sliding relationship between said first and second buckle parts, and said recess means have ends which open in a direction toward said belt second end and sloping slightly from a line normal to said belt second end in a direction toward said clamping means.

8. The tourniquet as defined in claim 1 wherein said recess means include a pair of recesses opening toward each other, each recess having an end, said pivot pin means include a pivot pin received in each recess end, said recesses each having a lower edge and said recess ends each having an upper edge, said upper and lower edges each being inclined at an acute angle to and below the horizontal converging in a direction from said clamping means toward said pivot pins, and the included angle of said recess lower edges to the horizontal is greater than the included angle of said recess ends upper edges to the horizontal.

9. The tourniquet as defined in claim 1 wherein said recess means opens in a direction toward said clamping means, said cam means includes a cam surface and a cam follower carried one each by said first and second buckle parts, and said cam surface being inclined in a generally downward direction toward said clamping means.

10. The tourniquet as defined in claim 1 wherein said recess means opens in a direction toward said clamping means, said cam means includes a cam surface and a cam follower carried one each by said first and second buckle parts, said cam surface being inclined in a generally downward direction toward said clamping means, said recess means is inclined at an acute angle to and below the horizontal converging in a direction from said clamping means toward said pivot pin means, and the acute angle included between said recess means and the horizontal is greater than the acute angle included between said cam surface and the horizontal.

11. The tourniquet as defined in claim 1 wherein said cam means are defined by a pair of spaced cam bars disposed transversely to a longitudinal axis of said belt.

12. The tourniquet as defined in claim 1 wherein said cam means are defined by a pair of spaced cam bars disposed transversely to a longitudinal axis of said belt, the spacing between said cam bars is less than the width of said belt, and said belt is transversely flexible to effect insertion or removal of said belt second end relative to said buckle by insertion and removal thereof through said spacing.

13. The tourniquet as defined in claim 1 wherein said belt first carries a spring tongue, said first buckle part has a tongue-receiving recess, and said spring tongue is releasably received in said tongue-receiving recess for normally precluding inadvertent disconnecting of said connecting means.

14. A tourniquet comprising a resilient belt and a buckle, said buckle having first and second buckle parts, means for connecting a first end of said belt to said first buckle part, means for releasably clamping a second end of said belt between said first and second buckle parts, a loop between said first and second belt ends, interengaged pivot pin and recess means for cooperatively slidably securing and releasing said first and second buckle parts and effecting pivotal movement therebetween, means for imparting relative pivotal movement between said first and second buckle parts to effect the clamping of said belt second end therebetween by said clamping means, said pivot pin means being positioned between said clamping means and said movement imparting means, said pivotal movement including opposing surfaces of said first and second buckle parts spaced a predetermined distance from each other between which said second belt end is positioned, and said belt has a thickness excluding said predetermined distance whereby the resilience of said belt effects the automatic relative pivoting of said first and second buckle parts and thereby clamp said second belt end by said clamping means.

15. The tourniquet as defined in claim 14 including a shallow recess adjacent a first of said opposing surfaces opposing a projecting surface portion of a second of said opposing surfaces resulting in a deflection of a portion of said belt therebetween.

16. The tourniquet as defined in claim 14 including a shallow recess adjacent a first of said opposing surfaces opposing a projecting surface portion of a second of said opposing surfaces resulting in a deflection of a portion of said belt therebetween, and said shallow recess and projecting surface portion are disposed generally centrally of the belt width.

17. The tourniquet as defined in claim 14 wherein said recess means is closed in a direction toward said cam means and open in a direction toward said clamping means.

18. The tourniquet as defined in claim 14 wherein said recess means is open in a direction toward said cam means and closed in a direction toward said clamping means.

19. The tourniquet as defined in claim 14 wherein said recess means is closed in a direction toward said cam means and open in a direction toward said clamping means, and said recess means is inclined at an acute angle to the horizontal converging in a direction from said clamping means toward said pivot pin means.

20. The tourniquet as defined in claim 14 wherein said recess means is closed in a direction toward said cam means and open in a direction toward said clamping means, and said recess means is inclined at an acute angle to and below the horizontal converging in a direction from said clamping means toward said pivot pin means.

* * * * *